(12) United States Patent  
Shao

(10) Patent No.: US 8,939,953 B2  
(45) Date of Patent: Jan. 27, 2015

(54) METHODS OF USING MULTILAYER MEDICAL SPONGES

(76) Inventor: Weiru Shao, Auburndale, MA (US)

( * ) Notice: Subject to any disclaimer, the term of this patent is extended or adjusted under 35 U.S.C. 154(b) by 349 days.

(21) Appl. No.: 13/548,086

(22) Filed: Jul. 12, 2012

(65) Prior Publication Data

US 2012/0283762 A1    Nov. 8, 2012

Related U.S. Application Data

(63) Continuation-in-part of application No. 12/949,761, filed on Nov. 18, 2010, now abandoned.

(60) Provisional application No. 61/394,320, filed on Oct. 18, 2010.

(51) Int. Cl.
| | | |
|---|---|---|
| *A61F 13/15* | (2006.01) | |
| *A61F 13/44* | (2006.01) | |
| *A61B 19/08* | (2006.01) | |
| *A61F 13/00* | (2006.01) | |
| *A61F 13/36* | (2006.01) | |
| *A61B 19/00* | (2006.01) | |

(52) U.S. Cl.
CPC ............... *A61F 13/44* (2013.01); *A61B 19/088* (2013.01); *A61B 2019/306* (2013.01); *A61F 2013/15073* (2013.01); *A61B 2019/304* (2013.01); *A61B 2019/305* (2013.01); *A61B 19/30* (2013.01); *A61F 13/00008* (2013.01); *A61F 13/00029* (2013.01); *A61F 13/00034* (2013.01); *A61F 13/00063* (2013.01); *A61F 13/36* (2013.01)
USPC ............................................ 604/356; 602/58

(58) Field of Classification Search
CPC ...... A61B 19/08; A61B 19/088; A61B 19/20; A61B 19/30; A61B 19/40; A61B 2019/081; A61B 2019/082; A61B 2019/208; A61B 2019/303; A61B 2019/304; A61B 2019/305; A61B 2019/306; A61F 13/00017; A61F 13/00029; A61F 2013/15073
USPC ...................................... 604/356, 370; 602/58
See application file for complete search history.

(56) References Cited

U.S. PATENT DOCUMENTS

| 3,911,922 A | 10/1975 | Kliger |
| 4,068,666 A | 1/1978 | Shiff |

(Continued)

OTHER PUBLICATIONS

American Surgical Company, "Our Products" web page, downloaded from www.amsurp.com/our-products.php#non-stix on Nov. 18, 2010.

*Primary Examiner* — Lynne Anderson  
(74) *Attorney, Agent, or Firm* — Douglas Denninger

(57) ABSTRACT

A method of protecting sensitive tissue from damage during a surgical procedure using at least one medical tool having a rotatable bit capable of removing tissue, including selecting a multilayer sponge having (i) a tissue-compatible layer with a tissue contact surface capable of being placed against the sensitive tissue, and (ii) a low-friction layer having a lower coefficient of friction than that of the tissue-compatible layer, being affixed to the tissue-compatible layer, and having an outward-facing surface including biocompatible material not easily worn away by brief contact with the rotatable bit during the surgical procedure. The method further includes placing the tissue contact surface of the biocompatible layer against sensitive tissue such that the outward-facing surface of the low-friction layer is positioned between the sensitive tissue and the rotatable bit to protect the sensitive tissue from damage and prevent the sponge from being drawn around the bit when it rotates.

15 Claims, 4 Drawing Sheets

(56) References Cited

U.S. PATENT DOCUMENTS

| | | |
|---|---|---|
| 4,430,013 A | 2/1984 | Kaufman |
| 4,961,735 A | 10/1990 | Siciliano |
| 4,994,049 A | 2/1991 | Latzke et al. |
| 5,112,325 A | 5/1992 | Zachry |
| 5,254,109 A | 10/1993 | Smith et al. |
| 5,460,621 A * | 10/1995 | Gertzman et al. ............ 604/358 |
| 5,466,231 A * | 11/1995 | Cercone et al. ............... 604/369 |
| 5,524,642 A | 6/1996 | Rosenblatt |
| 5,556,391 A | 9/1996 | Cercone et al. |
| 2006/0228511 A1 | 10/2006 | Bourdelais et al. |
| 2010/0298788 A1 | 11/2010 | Uematsu |
| 2012/0071846 A1 | 3/2012 | Shao et al. |

\* cited by examiner

METHODS OF USING MULTILAYER MEDICAL SPONGES

CROSS-REFERENCES TO RELATED APPLICATIONS

This application is a continuation-in-part application of U.S. application Ser. No. 12/949,761 filed Nov. 18, 2010 and also claims the benefit of U.S. Provisional Application No. 61/394,320 filed Oct. 18, 2010.

BACKGROUND OF THE INVENTION

1. Field of the Invention

This invention relates generally to protecting sensitive tissue from rotating instruments and more particularly to using medical sponges that are constructed with multiple layers.

2. Description of Related Art

Many medical procedures, including surgeries, are performed with the aid of rotating instruments such as drills and burrs. Frequently, drilling or grinding is conducted in close proximity to critical soft tissues, such as brain, blood vessels, and nerves. Working space in these surgeries is sometimes limited and may lead to accidental injuries. For example, a spinning drill bit removing bone may nick adjacent critical soft tissue, causing a potentially serious injury.

Techniques have been developed to protect against these hazards. These include placing medical sponges on top of critical structures. Sponges not only help to protect critical tissues, but they also help to maintain hydration during long operations.

The inventor has recognized that conventional medical sponges sometimes fall short in performing their protective functions. For example, spinning bits present a potential hazard. As is known, drill and grinder bits used in medical procedures may be composed of fluted metal or other materials, and may have roughened or abrasive surfaces. Some include abrasive particles such as diamond burr. All of these various drilling and grinding tools are collectively referred to herein as "bits." If a spinning bit accidentally touches a sponge, it may "catch" on the sponge, causing the sponge to become dislodged from its protective position and exposing the underlying tissues to damage. Certain bits intended for cranial, orthopedic and/or dental surgery typically rotate at 75,000 to 85,000 RPM (revolutions per minute). In some cases, the sponge may be caused to wrap around the drill bit and form a fast spinning ball of material. The size and speed of the spinning material may be enough to damage adjacent tissues.

BRIEF SUMMARY OF THE INVENTION

The inventor has recognized and appreciated that the safety of surgeries and other medical procedures may be improved by using a novel multilayer medical sponge. In accordance with one embodiment, the multilayer medical sponge includes at least two layers, a tissue-compatible layer and a low-friction layer. The tissue-compatible layer preferably is absorbent and is placed against sensitive tissues to cover them and provide hydration during medical procedures, whereas the low-friction layer faces away from these tissues to help protect them from damage resulting from various hazards, such as impingement of medical tools, including spinning drill or grinder bits, upon the multilayer sponge.

This invention features a method of protecting sensitive tissue from damage during a surgical procedure using at least one medical tool having a rotatable bit capable of removing tissue, including selecting a multilayer sponge having (i) a tissue-compatible layer with a tissue contact surface capable of being placed against the sensitive tissue, and (ii) a low-friction layer having a lower coefficient of friction than that of the tissue-compatible layer, being affixed to the tissue-compatible layer, and having an outward-facing surface including biocompatible material not easily worn away by brief contact with the rotatable bit during the surgical procedure. The method further includes placing the tissue contact surface of the biocompatible layer against sensitive tissue, especially sub-dermal tissue such as brain tissue, such that the outward-facing surface of the low-friction layer is positioned between the sensitive tissue and the rotatable bit to protect the sensitive tissue from damage and prevent the sponge from being drawn around the bit when it rotates.

In accordance with another embodiment, the multilayer sponge includes an absorbent tissue-compatible layer and a low-friction layer adjacent to the absorbent layer. Each layer has a surface facing outward. The outward-facing surface of the low-friction layer is substantially smoother than that of the absorbent layer. Preferably, the low-friction layer is visibly smooth and substantially free of fibers, more preferably completely free of fibers, while the tissue-compatible layer has a visibly perceptible texture. In some embodiments, the tissue-compatible layer includes fibrous material and protects the sensitive tissue from desiccation. In certain embodiments, the tissue-compatible layer is capable of providing hydration to the sensitive tissue during the surgical procedure.

In accordance with yet another embodiment, the low-friction layer is semi-rigid such that the sponge transitions from stiffness to flexibility with a transition radius of curvature of at least twice the radius of a bit selected for the surgical procedure. In some embodiments, the transition radius of curvature is about two mm to about one cm. In certain embodiments, the low-friction layer has a melting temperature greater than 300 degrees Celsius.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4A is a simplified view of a bit placed against a multilayer sponge having a transition radius of curvature at least twice the radius of the bit while

DETAILED DESCRIPTION OF THE INVENTION

Figure 1:
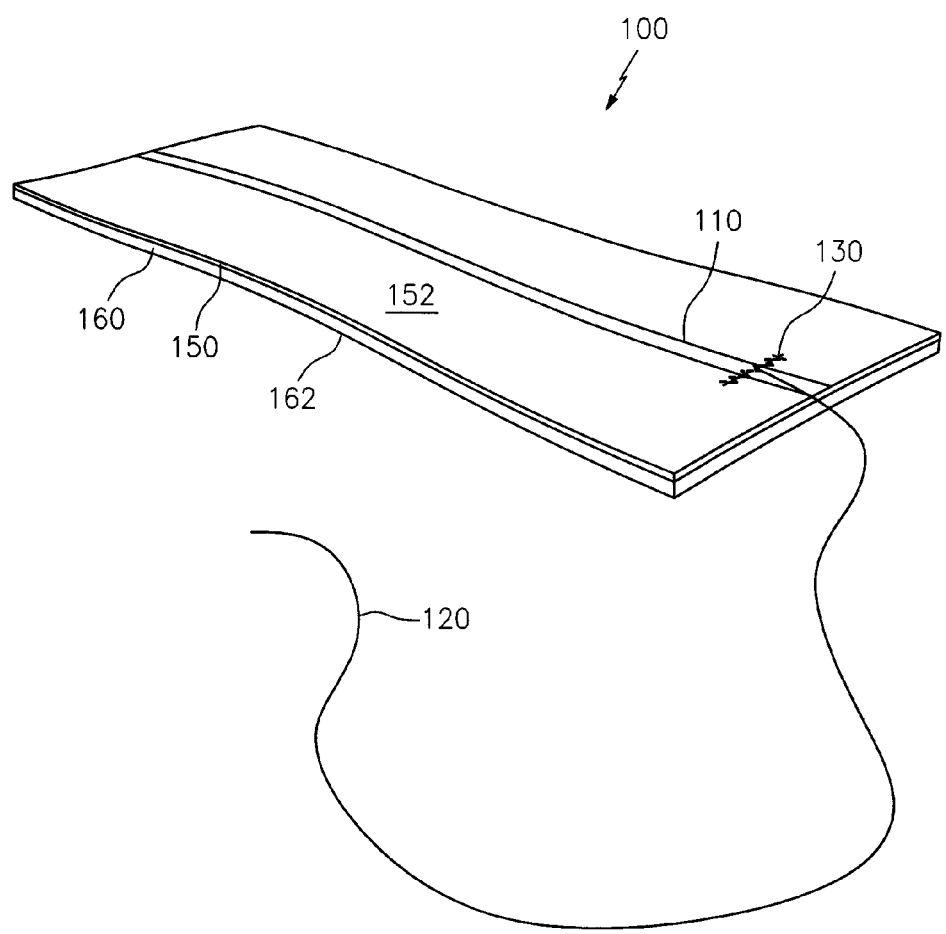
FIG. 1 is a perspective view of an exemplary multilayer medical sponge.

Techniques, including a preferred embodiment of the invention, are described herein-below for providing a multilayer medical sponge to help protect medical patients against injuries arising from various hazards such as contact with spinning drill bits and other tools or instruments. These techniques may be employed to make a multilayer medical sponge and to use a multilayer medical sponge to improve the safety of medical procedures.

This invention may be accomplished by protecting sensitive tissue, especially sub-dermal tissue such as brain tissue, from damage during a surgical procedure using at least one medical tool having a rotatable bit capable of removing tissue, including selecting a multilayer sponge having (i) a tissue-compatible layer with a tissue contact surface capable of being placed against the sensitive tissue, and (ii) a low-friction layer having a lower coefficient of friction than that of the tissue-compatible layer, being affixed to the tissue-compatible layer, and outward-facing surface, and including biocompatible material not easily worn away by brief contact with the rotatable bit during the surgical procedure. The method further includes placing the tissue contact surface of the biocompatible layer against the sensitive tissue such that the outward-facing surface of the low-friction layer is positioned between the sensitive tissue and the rotatable bit to protect the sensitive tissue from damage and prevent the sponge from being drawn around the bit when it rotates.

Preferably, a surgical sponge utilized according the present invention has substantially opposite friction properties between the two functional layers. In order to protect the underlying tissue that it lays on from desiccation and to aid surgical exposure, the tissue-compatible layer preferably is absorbent—i.e., capable of water retention and blood absorption—and relatively high friction so that it will not slide off the intended tissue location, even with a drill bit spinning at 75,000-85,000 RPM touching the low-friction layer. On the other hand, in order to prevent the sponge from getting caught by the spinning drill bit, the low-friction layer needs to have substantially low friction and local rigidity so that the spinning drill bit slides over the surface of the stationary sponge without snagging or catching the sponge. This unique design is accomplished by manufacturing the sponge with opposing friction properties between the tissue-compatible layer and the low-friction layer.

An amount of friction is determined by the contact area and the friction coefficient of the sponge material. For the tissue-compatible layer to maximize friction, a relatively large area that is practically allowed by surgery and a biocompatible material with high friction coefficient, like cotton, can be selected. If the material is made with fiber, either woven or non-woven, it may improve resistance. For the low-friction layer, a low friction coefficient material is needed, such as polytetrafluoroethylene (PTFE). Other suitable low-friction materials, preferably biocompatible and sufficiently flexible, include aluminum magnesium boride (BAM) and diamond-like carbon (DLC). At the same time, the contact area between the sponge and the drill bit has to be minimized. That is, the sponge needs to be sufficiently rigid at and near the contact point with the drill bit so that it will not deform excessively and then wrap around the bit. If there is too much contact, the friction between the bit and the sponge can draw the sponge around the bit. However, the sponge has to maintain overall flexibility so that it will easily fit into a restricted and often irregular surgical field, especially during key-hole operations such as through a cranium. In addition, the surgeon will move the spinning bit during drilling from one surgical field to another and the bit-sponge contact point shifts around. The sponge has to allow the shifting of the local stiff areas without repositioning. Therefore, the sponge needs local stiffness around the drill bit while at the same time to be flexible on a larger scale.

Figure 2:
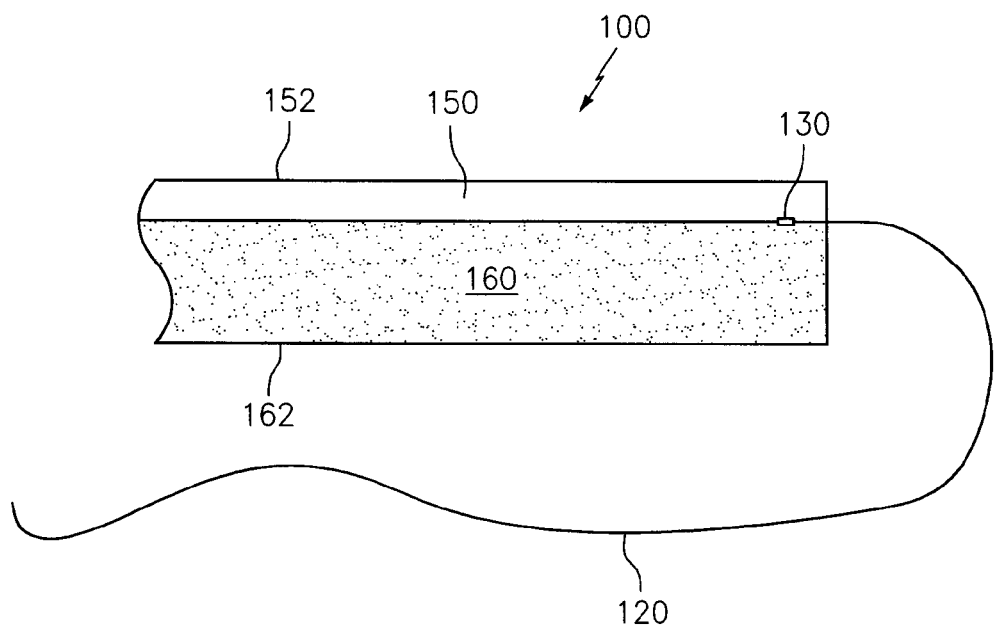
FIG. 2 is a side view of the exemplary multilayer medical sponge of FIG. 1.

FIGS. 1 and 2 show an exemplary multilayer medical sponge 100 which provides bit-resistant characteristics. The sponge 100 includes a first layer 160 and a second layer 150. The first layer 160 is made of an absorbent material in this construction and has an outward-facing surface 162. The second layer 150 is made of a low-friction, bit-resistant material and has an outward-facing surface 152. Optionally, a radiopaque marker 110 is applied to the sponge 100 and a string 120 is attached to the sponge using, for example, stitching 130 as shown in schematic cross-section in FIG. 2. The radiopaque marker 110 may be imbedded or painted within sponge 100, e.g., between the layers 160 and 150, for use in localizing and identifying the sponge 100 within a surgical field using x-rays. The string 120 may be applied in any suitable way, such as between the layers 160 and 150 or to the top or bottom of the sponge 100. The string 120 may assist in retrieving or relocating the sponge 100 during a procedure.

The layers 160 and 150 are affixed together; for example, they may be stitched together. Alternatively, they may be affixed by gluing, heating, melting, bonding, or ultrasonic welding, or by using any other suitable technique. The low-friction layer 150 may be also applied in a liquid or semi-liquid state, such as by rolling or spraying, and then allowed to dry or cure.

The absorbent tissue-compatible layer 160 preferably is made from a soft, biocompatible, absorbent material that is safe when placed in contact with sensitive tissues and is capable of retaining water for maintaining hydration of those tissues. It is also preferable for the tissue-compatible layer 160 to have a relatively high frictional engagement with sensitive tissue to minimize slippage. Non-limiting examples include cotton, gauze, rayon, silk, or polyester. Other materials may be used, and such materials are generally fibrous, porous, or both, to promote wicking action and absorption and retention of bodily fluids.

The low-friction layer 150 provides bit-resistant characteristics. In this manner, the low-friction layer 150 preferably is smoother and substantially more slippery than the absorbent layer 160. For example, the surface 152 preferably has a lower coefficient of friction with metal or diamond burr than the surface 162. The increased slipperiness of the low-friction layer 150 may help to prevent the sponge 100 from being dislodged by frictional contact with medical tools and instruments, such as spinning drill bits. The outer surface 152 of the low-friction layer may be substantially free of loose fibers, gaps, or other structures that are prone to cause entanglement with a spinning drill bit. More preferably, the outer surface 152 is completely free of fibers and other structures which may cause entanglement. Furthermore, a surface made from woven or non-woven fibers tends to have loose or projecting fibers as manufactured, as packaged and transported, and especially after placement sub-dermally and repositioning by forceps or other tools. These loose or projecting fibers (from manufacturing, packaging, manipulation before use, and instrumentation) are likely to be caught by a fast spinning drill bit and increases the chance that the sponge becomes wrapped around the bit, even if the surface has a low friction coefficient measured without the fibers loosened. Material with a foam or expanded structure also creates loose fibers, filaments, or chunks. Therefore, the low-friction layer preferably is a polymer with uniform and smooth surface and structure free of loose fibers. One example is a solid and compact PTFE sheet. Nylon fibers, PTFE fibers, and expanded PTFE (with a foam structure) are generally undesirable for low-friction layers according to the present invention.

Figure 4A:
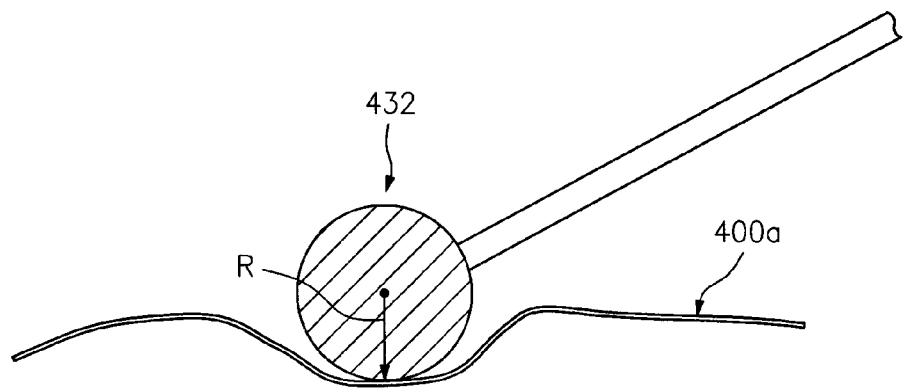

The low-friction layer 150 preferably causes the multilayer sponge 100 to be semi-rigid. In this context, "semi-rigid" means relatively flexible for radii of curvature above a certain transition level, but relatively stiff for radii of curvature below this transition level. The phrase "radius of curvature" or "radii of curvature" means a dimension of "curvature, or bending". As bending is attempted for increasingly smaller radii, a state will be reached where the sponge transitions from relative flexibility to relative stiffness. For example, when a sponge is used next to a drill bit with a diameter of 5 mm, the radius of curvature of the sponge preferably is at least 5 mm, that is, at least twice the bit radius of 2.5 mm, so that the sponge does not bend in the undesirable manner illustrated in FIG. 4B. In preferred constructions, the diameter of the drill bit is the minimal radius of sponge curvature. Twice the bit radius allows less contact between the bit and the sponge such as illustrated in FIG. 4A. In this example, the sponge is relatively stiff below 5 mm, i.e., it resists further bending under normal contact pressures. But for bending dimensions above 5 mm, that is, when the radius of attempted curvature is above 5 mm, the sponge is relatively flexible so it can be curled, twisted, and bent in normal use as long as the radius of attempted curvature is above 5 mm. Drill bits used for medical purposes typically have diameters in the range between 0.5 mm and 8 mm. Because the low-friction layer 150 causes the sponge 100 to be stiff on the scale of typical drill bits, the low-friction layer helps to prevent the sponge 100 from deforming easily around the drill bits and thereby being drawn around them to form spinning balls of material. At the same time, the semi-rigidity of the low-friction layer 150 allows the sponge 100 to remain pliable and compliant on larger scales. Therefore, the sponge 100 may still be draped over sensitive tissues and caused to readily conform to their shapes.

The degree of rigidity of the low-friction layer 150 may be varied based on the intended use, and different sponges 100 may be provided having different degrees of rigidity. For example, when using a sponge 100 in the vicinity of small drill bits, e.g., in the 0.8 mm range, a sponge 100 may be selected that has a low-friction layer 150 composed and sized so as to place the transition between stiffness and flexibility at a smaller radius, such as 2 mm. Conversely, when using a sponge 100 in the vicinity of large drill bits, e.g., in the 8 mm range, a different sponge 100 may be selected that has a low-friction layer 150 composed and sized so as to place the transition between stiffness and flexibility at a larger radius, such as 1 cm. In a very tight space, there is no room for a big drill bit and the sponge with large curvature radius may be too rigid to be bent to fit within. Therefore, a more flexible sponge with smaller curvature diameter in conjunction with a small drill bit is required. Nevertheless, a sponge with a transition radius of curvature larger than the bit diameter may still work if there is enough space to place the sponge, i.e., a 5 mm transition curvature sponge can work with a 3 mm bit. An assortment of sponges 100 having different transition radii may be provided.

In addition, the whole sponge preferably has enough elasticity to return to its original shape when external pressure is removed. During surgical drilling in tight and narrow spaces, the sponge is deformed into a curvature by the drill bit. The tissue underneath the sponge is compressed. After the drilling is completed and the bit is removed, the sponge preferably returns to its original shape to relieve the underlying tissue from compression. A malleable material with memory like aluminum foil is undesirable for techniques according to the present invention. As the drill bit is removed, aluminum foil would tend to maintain curvature that continues to compress underlying sensitive tissue for an extended and unintended period, potentially causing tissue ischemia and necrosis.

The low-friction layer 150 may also be tough. By "tough" it is meant that the low-friction layer 150 may not be easily worn away by brief contact with spinning drill bits. Once the low-friction layer 150 has been partly or completely worn away by repeated contact with a drill bit, medical personnel may replace the sponge 100 with a new one.

To provide drill-resistance, the low-friction layer 150 may be composed of materials having one or more of the above characteristics, i.e., smoothness, slipperiness, freedom from loose fibers or gaps, semi-rigidity, or toughness. Possibly suitable materials, depending on the procedure, include Gore-Tex®, nylon, Silastic®, and Teflon® PTFE. Some materials such as PTFE are more preferred for temperature resistance as described in more detail below.

The thickness of the low-friction layer 150 depends upon the materials used and the desired level of semi-rigidity. In one example, the low-friction layer 150 is made of Teflon PTFE and has a thickness of 0.06 mm. Using this material and thickness, a multilayer sponge 100 may be constructed having an overall dry thickness of 0.8 mm, which is approximately the same as the thickness of a conventional medical sponge. Therefore, the sponge 100 provides protective functions that are absent from conventional sponges without requiring much if any additional size or bulkiness. The fact that the sponge 100 may be made to be no larger than conventional sponges confers a great advantage in surgeries conducted in very small spaces.

When used in a surgical procedure, the multilayer sponge 100 may be inserted into a surgical field and placed against sensitive tissues with the absorbent layer 160 contacting the sensitive tissues, thereby allowing the absorbent layer 160 to cover and hydrate them. The low-friction layer 150 of the multilayer sponge 100 may face outwardly, away from the sensitive tissues. The low-friction layer 150 may thereby form a protective shield over the sensitive tissues to help guard them against intra-operative injury.

Figure 3A:
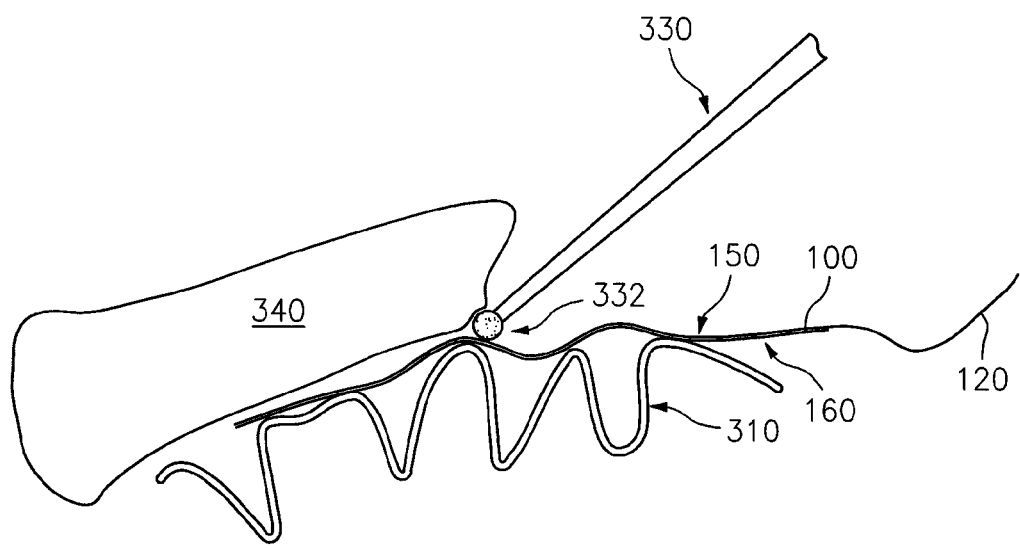
FIG. 3A is a simplified view of an exemplary medical procedure wherein the multilayer medical sponge of FIGS. 1-2 is placed over sensitive brain tissue.

FIG. 3A shows an example of a surgical procedure in which a multilayer sponge 100 may be employed to help to protect against damage from a surgical tool 330 having a rotatable drill bit 332. The sponge 100 may be inserted into a surgical field and placed directly over sensitive tissue, such as brain tissue 310. The sponge 100 may be placed with its absorbent layer 160 facing toward the brain tissue 310 and its low-friction layer 150 facing away from the brain tissue 310. The surgical procedure may require that certain portions of bone, such as skull bone tissue 340, located close to the brain tissue 310, be removed using the drill bit 332. With conventional sponges, this procedure may pose a risk that inadvertent contact between the spinning drill bit 332 and a conventional sponge would dislodge the sponge from its protective position and possibly cause the sponge to wrap around the drill bit 332 and form a dangerously spinning ball of material. However, with the multilayer sponge 100, this risk is significantly reduced. The tough, slippery, and/or semi-rigid qualities of the low-friction layer 150 of the multilayer sponge 100 enable it simply to yield to contact with the spinning drill bit 332 without becoming dislodged. Typically, the frictional forces between the absorbent layer 150 and the underlying tissue 310 are relatively high, especially when the absorbent layer 150 is wet, compared to the frictional forces between the drill bit 332 and the low-friction layer 150. Consequently, the sponge 100 tends to remain in place. Also, the semi-rigid quality of the low-friction layer 150 typically prevents the sponge 100 from deforming around the spinning drill bit 332 and becoming entangled.

Contact between the spinning drill bit 332 and the sponge 100 may cause localized heating within the sponge 100. During heavy surgical uses when the bit grinds the bone and slides on the resistant layer for a long period of time, it may generate intense heat above 300 degrees Celsius at the contact point between the drill and the low-friction layer, especially with diamond bits. It is preferable for the low-friction layer to have a melting temperature above 300 Celsius to prevent the low-friction layer from melting and thus failing. The tissue-compatible layer can prevent heat injury to underneath tissue by insulation and by heat transfer to water which it is saturated with, as long as the low-friction layer stay in place. PTFE has a melting point of 327 Celsius and is suitable for this purpose. Solid nylon with a melting point of 256 Celsius, polyethylene with a melting point of 130 Celsius, polyvinyl chloride with a melting point below 260 Celsius are generally undesirable for sponges utilized according to the present invention. Further, the sponge preferably is free of chemicals, dye, or drugs that may decompose or are unstable above body temperature. If there are drugs added to the sponge, their release to the body should not be affected by body fluids, irrigation, and temperature. However, the degree of heating is much less than with conventional sponges due to slipperiness of the low-friction layer 150. Also, since the low-friction layer 150 is adjacent to and generally in direct contact with the wet absorbent layer 160, heat is quickly drawn away from the point of contact and dispersed, posing little risk of harm. If a medical procedure results in repeated or frequent contact between the drill bit 332 and the sponge 100, medical personnel may be well advised to replace the sponge 100, or at least to inspect the low-friction layer 150 for signs of wear before exposing the sponge 100 to additional contact with the drill bit. It is understood, therefore, that the bit-resistant quality of the low-friction layer 150 is not intended to be absolute but rather relative and significantly improved as compared with that of conventional sponges.

Figure 3B:
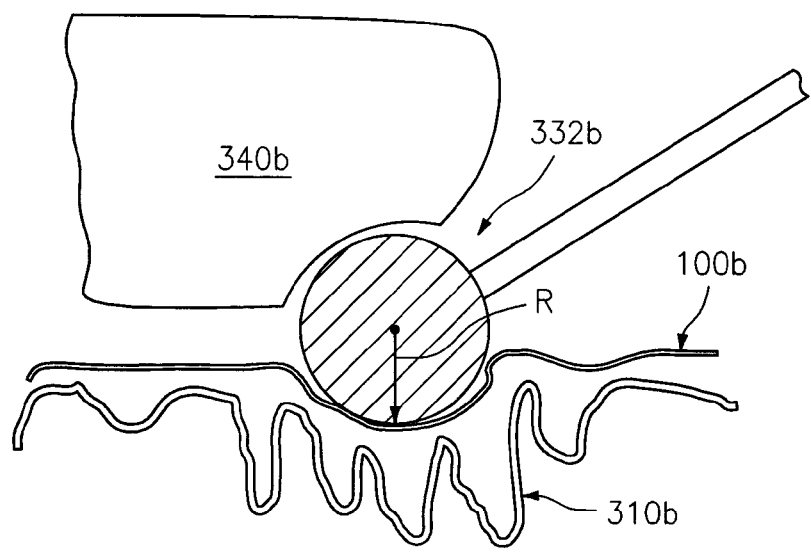
FIG. 3B is an enlarged view similar to FIG. 3A showing the radius of curvature of the sponge relative to the radius of the bit.

FIG. 3B provides a schematic cross-sectional view of a rotatable bit 332b having a radius R engaging bone 340b while pressing against sponge 100b above tissue 310b.

Figure 4B:
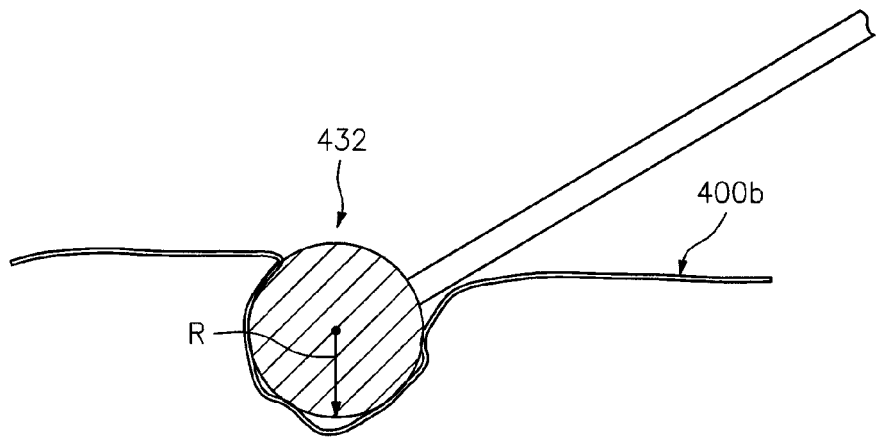
FIG. 4B is a similar view showing a multilayer sponge have a transition radius of curvature less than twice the bit radius.

A bit 432 is shown in cross-section in FIGS. 4A and 4B relative to sponges 400a and 400b, respectively, with bone and sensitive tissue omitted for ease of illustration. The transition radius of curvature of sponge 400a is greater than twice the radius R of bit 432 and thus is suitably matched for procedures according to the present invention. In contrast, sponge 400b has a transition radius of curvature less than twice radius R and is prone to bit 432 being pressed more than half way into sponge 400b as illustrated in FIG. 4B. Sponge 400b therefore is generally unsuitable for use with bit 432.

The materials used to construct the multilayer sponges 100, 100a, 400a, and 400b are preferably biocompatible, non-toxic and free of any substances that may cause negative tissue reactions. When the sponges are used in the proximity of spinning drill bits, it is expected that a small volume of fine debris may be ejected from the sponges. Some of this fine debris may remain in the patient's body after surgery. Therefore, it is important to the long-term health of patients that the materials of the sponges elicit no ill effects, either in the short term or in the long term.

Preferably, the multilayer medical sponges 100, 100a, 400a, and 400b are provided in a range of sizes and shapes, as desired for different medical uses. Typically, sponges are rectangular and range in size from 0.5 cm by 1 cm to 2 cm by 10 cm, although these are merely examples. Sponges may be provided in any suitable size and shape.

Having described certain embodiments, numerous other embodiments or variations can be made. For example, the low-friction layers of the multilayer sponges 100, 100a, 400a and 400b may be both bit-resistant and laser-reflective. Also, the low-friction layers of the various multilayer sponges may be resistant to other potentially harmful agents besides drill bits and laser light. For example, they may protect against contact with medical tools such as scalpels and probes. In addition, the low-friction layers of the various sponges may help to protect or shield against debris such as bone chips produced by saws, drills, or other equipment. The same characteristics that allow the multilayer sponges to be bit-resistant may also provide protection against other potentially harmful agents.

As shown and described, the layers and sublayers of each of the multilayer sponges 100, 100a, 400a, and 400b are aligned with other layers of the respective sponges and have the same perimeters and areas. This is merely an example. Alternatively, one layer may be made to be intentionally larger or smaller than another layer. For instance, the low-friction layers may be made to overhang the edges of the absorbent layers to help protect the edges of the absorbent layers from drills, laser light, and/or other potentially harmful agents. Also, the absorbent layers 160 may be made to extend beyond the boundaries of the respective low-friction layers to allow for increased fluid absorption or other benefits.

One may surmise that the low-friction layers are non-porous and impermeable. Although this may be the case in some instances, it is not required. For example, the low-friction layers may be composed of porous materials, or they may be perforated to allow them to "breathe" and exchange gases with their surroundings. Any pores or perforations in bit-resistant layers may be much smaller than the diameters of the drill bits with which the sponges are used, to prevent the drill bits from "catching" on the pores or perforations. Also, although the sponges are described in connection with certain surgeries, they may be used in any medical procedure that employs sponges.

Also, it is understood that the layers of material need not be made from solid sheets. For example, the material used to form the low-friction layer may be sprayed, rolled, painted, powder coated, or evaporated onto an absorbent layer, or it may be applied in some other way. Also, the low-friction layer may be provided as a sticky liquid sheet. The absorbent material may then be applied to the low-friction layer as a solid sheet or blown on as loose particles that adhere to the low-friction layer.

Further, it is not strictly required that the different layers or sublayers be formed from different materials. For example, they may be formed from a single material that is treated differently on its opposing surfaces. For instance, a material such as polyester may be provided in the form of a fibrous sheet. During fabrication, one side of the sheet could be kept cool while the other side is heated. The heated side could be allowed to melt to form a smooth, slippery surface, while the cool side is maintained in a cool state to remain fibrous and absorbent.

Although certain embodiments are disclosed herein, it is understood that these are provided by way of example only and the invention is not limited to these particular embodiments. Those skilled in the art will therefore understand that various changes in form and detail may be made to the embodiments disclosed herein without departing from the scope of the invention.

Various aspects of the present invention may be used alone, in combination, or in a variety of arrangements not specifically discussed in the embodiments described in the foregoing. The invention is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of protecting sensitive tissue from damage during a surgical procedure using at least one medical tool having a rotatable bit capable of removing tissue, comprising:
    selecting a multilayer sponge having (i) a tissue-compatible layer with a tissue contact surface capable of being placed against the sensitive tissue, wherein the tissue contact surface of the tissue-compatible layer has a visibly perceptible texture and includes fibrous material, and (ii) a low-friction layer having a lower coefficient of friction than that of the tissue-compatible layer, being affixed to the tissue-compatible layer, and having an outward-facing surface including biocompatible material not easily worn away by brief contact with the rotatable bit during the surgical procedure; and
    placing the tissue contact surface of the tissue-compatible layer against the sensitive tissue such that the outward-facing surface of the low-friction layer is positioned between the sensitive tissue and the rotatable bit to protect the sensitive tissue from damage and prevent the sponge from being drawn around the bit when it rotates.

2. The method of claim 1 wherein the low-friction layer is semi-rigid such that the sponge transitions from stiffness to flexibility at a transition radius of curvature of about two mm to about one cm.

3. The method of claim 1 wherein the low-friction layer has a melting temperature greater than 300 degrees Celsius.

4. The method of claim 1 wherein the low-friction layer includes polytetrafluoroethylene.

5. The method of claim 1 wherein the outward-facing surface of the low-friction layer is visibly smooth and substantially free of fiber.

6. The method of claim 1 wherein the tissue-compatible layer is absorbent and protects the sensitive tissue from desiccation.

7. The method of claim 6 wherein the tissue-compatible layer is capable of providing hydration to the sensitive tissue during the surgical procedure.

8. A method of protecting sensitive sub-dermal tissue from damage during a surgical procedure using at least one medical tool to drive a rotatable bit capable of removing tissue, comprising:
    selecting a rotatable bit having a first radius for a tissue engagement surface;
    selecting a multilayer sponge having (i) a tissue-compatible layer including absorbent material with a tissue contact surface capable of being placed against the sensitive tissue, wherein the tissue contact surface of the tissue-compatible layer has a visibly perceptible texture and includes fibrous material, and (ii) a low-friction layer having a lower coefficient of friction than that of the tissue-compatible layer, being affixed to the tissue-compatible layer, having an outward-facing surface including biocompatible material not easily worn away by brief contact with the rotatable bit during the surgical procedure, and being semi-rigid such that the sponge transitions from stiffness to flexibility at a transition radius of curvature of at least twice the first radius; and
    placing the tissue contact surface of the tissue-compatible layer against the sensitive tissue such that the outward-facing surface of the low-friction layer is positioned between the sensitive tissue and the rotatable bit to protect the sensitive tissue from damage.

9. The method of claim 8 wherein the low-friction layer has a melting temperature greater than 300 degrees Celsius.

10. The method of claim 9 wherein the low-friction layer includes polytetrafluoroethylene.

11. The method of claim 8 wherein the outward-facing surface of the low-friction layer is visibly smooth and substantially free of fiber.

12. The method of claim 9 wherein the tissue-compatible layer protects the sensitive tissue from desiccation.

13. The method of claim 12 wherein the tissue-compatible layer is capable of providing hydration to the sensitive tissue during the surgical procedure.

14. A method of protecting sensitive brain tissue from damage during a surgical procedure using at least one medical tool to drive a rotatable bit having a first radius for a tissue engagement surface capable of removing bone tissue, comprising:
    accessing the sensitive brain tissue during the surgical procedure;
    selecting a multilayer sponge having (i) a tissue-compatible layer including absorbent, fibrous material with a tissue contact surface capable of being placed against the sensitive tissue, and (ii) a low-friction layer having a lower coefficient of friction than that of the tissue-compatible layer, being affixed to the tissue-compatible layer, having an outward-facing surface that is visibly smooth and includes biocompatible material not easily worn away by brief contact with the rotatable bit during the surgical procedure, having a melting temperature greater than 300 degrees Celsius, and being semi-rigid such that the sponge transitions from stiffness to flexibility at a transition radius of curvature of at least twice the first radius; and
    placing the tissue contact surface of the tissue-compatible layer against the sensitive tissue such that the outward-facing surface of the low-friction layer is positioned between the sensitive tissue and the rotatable bit to protect the sensitive tissue from damage.

15. The method of claim 14 wherein the transition radius of curvature is about two mm to about one cm.

* * * * *